US009784680B2

(12) United States Patent
Lopez Quintela (10) Patent No.: US 9,784,680 B2
(45) Date of Patent: Oct. 10, 2017

(54) LUMINESCENT NANOSYSTEMS (75) Inventor: Manuel Arturo Lopez Quintela, Santiago de Compostela (ES)

(73) Assignee: UNIVERSIDADE DE SANTIAGO DE COMPOSTELA, Santiago de Compostela (ES)

( * ) Notice: Subject to any disclaimer, the term of this patent is extended or adjusted under 35 U.S.C. 154(b) by 158 days.

(21) Appl. No.: 14/123,149

(22) PCT Filed: Jun. 14, 2012

(86) PCT No.: PCT/EP2012/061305
§ 371 (c)(1),
(2), (4) Date: Nov. 29, 2013

(87) PCT Pub. No.: WO2012/172002
PCT Pub. Date: Dec. 20, 2012

(65) Prior Publication Data
US 2014/0106465 A1    Apr. 17, 2014

Related U.S. Application Data (60) Provisional application No. 61/524,311, filed on Aug. 16, 2011.

(30) Foreign Application Priority Data

Jun. 15, 2011 (EP) .................................. 11382196

(51) Int. Cl.
*G01N 21/64* (2006.01)
*C09K 11/02* (2006.01)
(Continued)

(52) U.S. Cl.
CPC .......... *G01N 21/6428* (2013.01); *B82Y 15/00* (2013.01); *C09K 11/025* (2013.01);
(Continued)

(58) Field of Classification Search
CPC .. G01N 21/6428; G01N 33/432; G01N 3/542; G01N 33/582; G01N 33/5432;
(Continued)

(56) References Cited

U.S. PATENT DOCUMENTS

2002/0021003 A1   2/2002   McGrew
2008/0265176 A1  10/2008   Chauhan et al.
2009/0035852 A1   2/2009   Lopez Quintela et al.
2011/0305919 A1  12/2011   Conroy et al.

FOREIGN PATENT DOCUMENTS

IN  WO 2012090034 A1 * 7/2012 ............. B82Y 30/00
JP     2009507996 A    2/2009
WO    2004003558 A1    1/2004
WO    2010016803 A1    2/2010

OTHER PUBLICATIONS

Douliez, J., et al., "Synthesising gold nanoparticles within bola fatty acid nanosomes", "Journal of Colloid and Interface Science", May 27, 2009, pp. 610-613, vol. 337.
(Continued)

*Primary Examiner* — David Porta
*Assistant Examiner* — Gisselle Gutierrez
(74) *Attorney, Agent, or Firm* — Hultquist, PLLC; Steven J. Hultquist (57) ABSTRACT The present invention relates to nanosystems comprising metal atomic quantum clusters (AQCs) of at least two different sizes encapsulated in a cavity with an inner diameter less than or equal to 10 nm for the use thereof as luminescent nanosystems, particularly for the use thereof as fluorescent nanosystems; as well as the method for obtaining and detecting them. The invention also relates to the use of said luminescent nanosystems as a fluorescent probe, biomarker or contrasting agent.

15 Claims, 5 Drawing Sheets

(51) Int. Cl.
*C09K 11/58* (2006.01)
*G01N 33/58* (2006.01)
*G01N 33/542* (2006.01)
*G01N 33/543* (2006.01)
*B82Y 15/00* (2011.01)

(52) U.S. Cl.
CPC ............ *C09K 11/58* (2013.01); *G01N 33/542* (2013.01); *G01N 33/5432* (2013.01); *G01N 33/582* (2013.01)

(58) Field of Classification Search
CPC .... G01N 33/542; B82Y 15/00; C09K 11/025; C09K 11/585; C09K 11/5853; C09K 11/58
USPC ................ 250/361 R, 459.1, 458.1; 436/172
See application file for complete search history.

(56) References Cited

OTHER PUBLICATIONS

Groehn, F., et al., "Nanoparticle Formation within Dendrimer-Containing Polymer Networks: Route to New Organic-Inorganic Hybrid Materials", "Macromolecules", Mar. 2, 2001, pp. 2179-2185, vol. 34.
Zheng, J., et al., "Highly Flourescent, Water-Soluble, Size-Tunable Gold Quantum Dots", "Physical Review Letters", Aug. 13, 2004, pp. 77402-1-77402-4, vol. 93, No. 7.

\* cited by examiner

LUMINESCENT NANOSYSTEMS

FIELD OF THE INVENTION

The present invention relates to nanosystems comprising metal atomic quantum clusters (AQCs) for the use thereof as luminescent nanosystems, particularly for the use thereof as fluorescent nanosystems.

BACKGROUND

Today, the use of fluorescence techniques such as fluorescence spectroscopy, fluorescence microscopy, flow cytometry or in vivo fluorescence imaging, allows the fast, clear, reliable and simple detection of the interaction between biomolecules, or the interaction of these biomolecules with other inorganic or organic molecules, such as drugs, for example. These techniques require the measurement of certain experimental parameters such as the excitation wavelength ($\lambda_{exc.}$), the emission wavelength ($\lambda_{em.}$), the intensity or quantum yield, the mean lifetime, and the fluorescence anisotropy.

A fluorescent probe suitable to be used as a nanosensor or bioprobe in drug discovery, genetic analysis, flow cytometry or high performance screening should have the following properties: it must be able to be excited without affecting the matrix it surrounds, easily detected, has a high quantum yield, is adaptable to the medium, for example, a cell culture, is stable and has functional groups which allow molecular labeling. It can also be favorable for these luminescent probes to have a long mean lifetime, to be non-toxic and that the luminescence parameters thereof are reproducible over time.

Today, the only fluorescent systems known having huge Stokes shifts of greater than 200 nm and slow decaying times of more than a microsecond are based on rare earth ions. However, they present multiple drawbacks such as: the difficulty in incorporating the same in matrices such that they do not lose their fluorescent characteristics; the existence of fixed and particular excitation, emission and Stokes shift characteristics corresponding to each rare earth, therefore they are not susceptible to being changed, and they are expensive and scarce materials. Examples of these systems are described in Sardar, D. K. et al., *Biophotonics*, January 2008; Resch-Genger, U., *Advanced Fluorescence Reporters in Chemistry and Biology II Springer Series on Fluorescence*, 2010, Volume 9, Part 1, 3-40; Harma H. et al., *Analytical Chemistry*, 2005, 77, 2643-2648; U.S. Pat. No. 7,465,747B2; US 2010/0224831 A1 and U.S. Pat. No. 4,283,382.

Therefore, it would be necessary to find luminescent probes that overcome these drawbacks of the nanoparticles based on rare earth elements.

BRIEF DESCRIPTION OF THE INVENTION

Surprisingly, the authors of the present invention have discovered fluorescent nanosystems with huge Stokes' shifts and decaying times much greater than those described in the state of the art which do not use rare earth elements. These nanosystems comprise an inner cavity, or nanocavity, where metal atomic quantum clusters (AQCs) of at least two different sizes preferably of transition metals are encapsulated. The inner surface of this inner cavity is functionalized to enable suitably stabilizing the AQCs and said cavity has a nanometric inner diameter allowing the distance between the AQCs of at least two different sizes present in said nanocavity to be less than or equal to approximately 10 nm. Without being bound to any particular theory, it is believed that this allows it to give Förster resonance energy transfer (FRET) producing luminescence. Since these nanocavities have an inner diameter smaller than the Förster distance, a distance less than or equal to 10 nm, and given that only active species are present in said nanocavities, the deactivation of luminescence particularly of fluorescence is prevented, being able to achieve with these systems high quantum yields which are greater than those obtained with the rare earth-based systems.

The excitation and emission wavelengths depend on the size of the AQCs present in the nanocavity of the nanosystem. Therefore, the excitation and emission wavelengths can be selected at will directing the formation of AQCs of necessary sizes so that FRET is given between the AQCs of at least two different sizes in said nanocavity. To optimize the FRET, the emission wavelength ($\lambda_{em.}$) of the small AQC or the smaller sized AQC which is the AQC that acts like a donor must be overlapped, as much as possible, with the excitation of the large AQC or the larger sized AQC which is the AQC that acts like an acceptor. Thus the Stokes shift to be obtained can be selected at will, thus releasing the fixed and particular imposition that exists in rare earth-based fluorescence methods. Furthermore, due to the characteristics of the AQCs used there is no photobleaching and the use of the FRET process as the basis of the proposed method ensures long fluorescence decaying times of more than a microsecond.

Metal transition elements such as Au or Ag, for example, which are not toxic when present in very low concentrations, can be used. Furthermore, the great natural abundance of these elements makes this a completely sustainable method. The luminescent nanosystems synthesized:

- are stable without loss of their properties over a period of at least one year stored under natural light and room temperature,
- are stable in the pH range of 3 to 10,
- can be concentrated until dry without losing their fluorescents properties even in dried form,
- can be redissolved once dried without losing their fluorescents properties, and also
- are used at a concentration less than that used in rare earth element-based luminescent systems.

The nanosystem can be further functionalized in its outer surface for the use thereof in different environments.

Therefore, an aspect of the present invention relates to the use of a nanosystem comprising metal atomic quantum clusters (AQCs) of at least two different sizes encapsulated in a cavity with an inner diameter less than or equal to 10 nm, preferably less than or equal to 5 nm as a luminescent nanosystem.

Another aspect of the present invention is the method for detecting said fluorescent nanosystems.

An additional aspect relates to the nanosystems per se comprising atomic quantum clusters (AQCs) of at least two different sizes encapsulated in a cavity with an inner diameter less than or equal to 10 nm wherein the metal of the AQCs is a transition metal, with the exception of Au, or a combination of transition metals.

Another aspect of the invention relates to the method for obtaining nanosystems comprising atomic quantum clusters (AQCs) of at least two different sizes encapsulated in a cavity with an inner diameter less than or equal to 10 nm, preferably less than or equal to 5 nm, wherein the metal of the AQCs is a transition metal with the exception of Au or a combination of transition metals.

DETAILED DESCRIPTION OF THE INVENTION

The meanings of the following terms of the present invention are detailed below.

The term "nanosystem" refers to an spheroid-like nanometric supramolecular structure formed by one or two layers of amphiphilic molecules, wherein said amphiphilic molecules form a nanocavity at the inside of the nanosystem. Particularly, the nanosystem having an outer diameter approximately equal to or less than 20 nm, preferably equal to or less than 18 nm and more preferably equal to or less than 15 nm. The inside of the nanosystem comprised at least one nanocavity with an inner diameter less than or equal to 10 nm, preferably less than or equal to approximately 5 nm, more preferably between 0.8 and 4 nm. In a particular embodiment, the inner diameter of the nanocavity is between approximately 1.5-1.8 nm. Non-limiting examples of nanosystems are nanosomes, micelles, reverse micelles, nanoemulsions or microemulsions.

The expression "spheroid-like" means that it has a solid geometrical figure similar in shape to a sphere.

The amphiphilic molecules forming the nanosystems may be the same or different, preferably two different type of molecules, and each molecule possess both hydrophilic and lipophilic properties.

The lipophilic properties are given by a group which is typically a hydrocarbon moiety, such as an aliphatic chain of the form $CH_3$-$(CH_2)_n$— or —$(CH_2)_n$— being 30>n>2, preferably 20>n>10.

The hydrophilic properties are given by a hydrophilic group. The hydrophilic group may be a charged group or a polar uncharged group. The charged group is selected from anionic groups, preferably is selected from the group formed by carboxylates, sulfates, sulfonates and phosphates. The polar uncharged group is selected from the group formed by —OH, —SH, —$NH_2$, —NH—, —Cl, —$PH_3$, —SR, —OR, —$NR_2$, —NHR and —NR—, wherein R represents an organic alkyl group of a short hydrocarbon chain, $C_1$-$C_4$, preferably methyl, ethyl or propyl group.

The amphiphilic molecules may have one aliphatic $CH_3$—$(CH_2)_n$— chain and one hydrophilic group bound to it or two hydrophilic groups bound each one at each end of the aliphatic —$(CH_2)_n$— chain.

The term "nanosome" in the scope of the present invention relates to a nanometric sized vesicle artificially prepared and formed by a lipid layer. Thus, the term "nanosome" refers to an spheroid nanometric supramolecular structure formed by one layer of amphiphilic molecules (lipids) having two hydrophilic groups bound each one at each end of the aliphatic —$(CH_2)_n$— chain, or at the antepenultimate, $\chi$, or penultimate, $\psi$, positions of the aliphatic $CH_3$—$(CH_2)_n$— chain.

Figure 2:
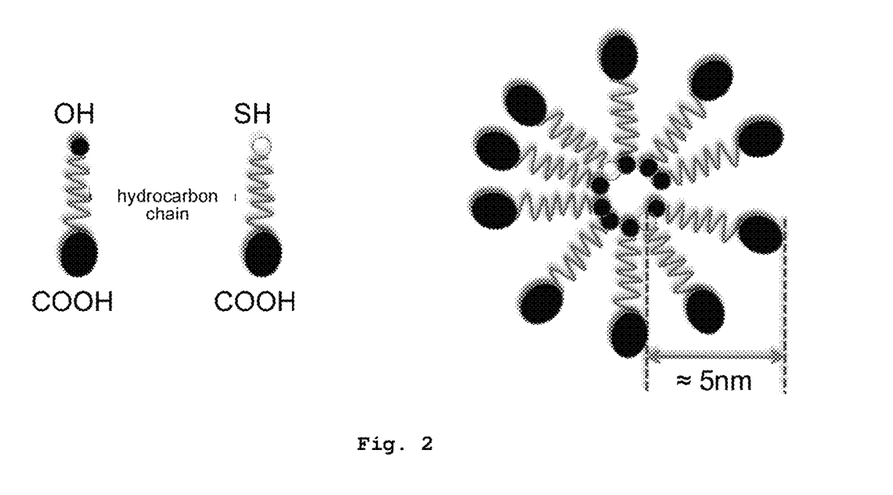
FIG. 2 shows a schematic depiction of the nanosystem particularly a nanosome where the ω-hydroxyacids and ω-mercaptoacids form the monolayer of the nanosome wherein the monolayer has an approximate thickness of 5 nm, it is observed that the acid groups form the outer surface of the nanosome and the hydroxyl, OH, and mercapto, SH, groups face inwards forming the surface of the inner cavity of the nanosome.

Therefore, the lipids forming said monolayer in the nanosomes of the invention comprise (see FIG. 2):

a hydrophilic group such as a carboxyl ($COO^-$) or phosphate ($PO_4^-$) group, for example, that are on the outer surface of the vesicle, at one end of the aliphatic chain and substituted at the antepenultimate, $\chi$, penultimate, $\psi$, positions of the aliphatic $CH_3$—$(CH_2)_n$— chain, or last, ω, positions of the aliphatic —$(CH_2)_n$— chain with groups such as for example —OH, —SH, —$NH_2$, —NH—, —Cl, —$PH_3$, —SR, —OR, —$NR_2$, —NHR, or —NR—, wherein R represents an organic group of a short hydrocarbon chain, $C_1$-$C_4$, capable of forming nanosomes which are located towards the inside of the vesicle, at the other end of the aliphatic chain or at the ultimate positions of said aliphatic chain with respect to hydrophilic group, said groups forming the nanocavity with an inner diameter less than or equal to 10 nm, preferably less than or equal to approximately 5 nm, more preferably between 0.8 and 4 nm. In a particular embodiment, the inner diameter of the nanocavity is between approximately 1.5-1.8 nm.

The term "micelle" refers to amphiphilic molecules aggregates. In an aqueous medium, the lipophilic domains of the molecule aggregate are oriented towards the inside of the micelle and the hydrophilic domains are in contact with the medium. In "reverse micelles" the molecules are organized such that the lipophilic region is exposed to the outside and the hydrophilic region to the inside. In the state of the art the term "microemulsion" is also used to refer to a "reverse micelle", i.e. the "microemulsion" is a particular embodiment of a "reverse micelle". The term "microemulsion" refers to a system of at least three components (water, organic solvent-known commonly as oil- and amphiphilic compound), single phase and thermodynamically stable, formed by nanometric sized droplets. Although not restrictive, the use of water-in-oil microemulsions wherein water droplets are dispersed in the organic medium is of particular interest for the present invention. Among these water-in-oil microemulsions, the use of polymerized microemulsions relating to microemulsions containing acrylic monomers, for example acrylamide or 1,6-hexanediol diacrylate inside the water droplets which are polymerized by means of introducing some initiator, such as for example a radical photoinitiator, is also of interest due to its stability. Thus, the microemulsion droplets can become more resistant.

The term "nanoemulsion" refers to a system of at least three components (water, organic solvent and stabilizing compound), two-phase and thermodynamically unstable but is temporary stabilized by chemical or physical processes and is formed by nanometric droplets. The formation of nanometric droplets is the only thing that differentiates the nanoemulsions from the emulsions known in the state of the art, therefore the term "nanoemulsion" generally refers to an emulsion in which the droplets are of nanometric size.

In a particular embodiment the nanosystem is selected from the group formed by nanosome, micelle and reverse micelle, preferably the nanosystem is a nanosome.

In the particular embodiment wherein the nanosystem is a nanosome, the nanosome comprises ω-hydroxyacids (HO—$(CH_2)_m$—COOH) and ω-mercaptoacids (HS—$(CH_2)_p$—COOH) where m and p have a value between 2 and 30, preferably m and p have a value between 10 and 20. In a particular embodiment m and p have a value of 15. The value of m and p can be different or the same. In the event that m and p are different the difference between them is less than 6 carbons, preferably the difference of the values of m and p is between 1 and 4. In a preferred embodiment m and p are the same. The ω-hydroxyacids and ω-mercaptoacids present in the nanosome are forming a spherical monolayer with the acid groups, —COOH, (or —COO$^-$, if the salt of the corresponding acid is used) directed towards the outer surface of the nanosystem and the —OH and —SH groups directed towards the inside forming an inner cavity in the nanosome such that two approximately concentric spheres are formed, or as referred to in the literature, in the form of fatty acids "bola". This spherical monolayer can have a thickness between approximately 2-10 nm, preferably approximately 5 nm.

In the particular embodiment wherein the nanosystem is a reverse micelle, the reverse micelle comprises at least two different surfactants, wherein at least one comprises a thiol or thioether group as its polar group. In a more particular embodiment, the at least two surfactants are an alcohol ethoxylate and a ω-mercaptoacid.

The inner cavity of the nanosystem is closed. As mentioned above, the inner diameter of said inner cavity is less than or equal to 10 nm, preferably less than or equal to approximately 5 nm and more preferably the inner diameter of said inner cavity is between approximately 0.8 and 4 nm. In a particular embodiment the diameter of this inner nanocavity is between approximately 1.5-1.8 nm. In the particular embodiment of the nanosomes, said nanocavity is formed by hydroxyl, —OH, and mercapto, —SH groups, however exchanging these functional groups with others that also interact with the metals, such as —$NH_2$, —NH—, —Cl, —$PH_3$, —SR, —OR, —$NR_2$, —NHR, —NR—, where R represents an organic group of a short hydrocarbon chain, $C_1$-$C_4$ capable of forming nanosomes, is possible.

A particular example of these nanosomes is described in Gaillard, C., *Journal of Colloid and Interface Science*, Vol. 337, 2, 610-613, which describes gold particle synthesis inside these nanosystems.

The term "Atomic Quantum Cluster", abbreviated as AQC, is understood, as said before, as metal Atomic Quantum Cluster. Metal Atomic Quantum Clusters are formed exclusively by zero-oxidation-state metal atoms, $M_n$, with less than 200 metal atoms ($M_n$, n<200) and with a size of less than 2 nm. The AQCs are stable over time.

The nanosystem described comprises, inside the inner cavity thereof, i.e., encapsulated, atomic quantum clusters, which are known for being a family of zero-valent metals which do not longer behave like a "metal" and their behaviour becomes molecular like. Therefore, new properties which are not observed in the nanoparticles, microparticles or metal materials in mass appear in these clusters. Therefore, the physical-chemical properties of the AQC cannot be simply extrapolated from those of the nano/microparticles.

In the present invention said AQCs encapsulated inside the mentioned inner cavity are formed by metal elements, $M_n$, of transition metals or the bimetal combinations thereof and are present in the nanosystem in at least two different sizes where n is the number of metal atoms present, n has a value of:

between 2 and 309 metal atoms ($M_n$, $2 \le n \le 309$),
between 2 and 102 metal atoms ($M_n$, $2 \le n \le 102$),
between 2 and 55 metal atoms ($M_n$, $2 \le n \le 55$), or
between 2 and 25 metal atoms ($M_n$, $2 \le n \le 25$).

The AQCs of the invention have sizes comprised between approximately 0.3 and 2.2 nm, preferably between approximately 0.3 and 2 nm, more preferably between approximately 0.3 and 1.8 nm.

One embodiment of the present invention relates to the use of a nanosystem as described above which comprises atomic quantum clusters (AQCs) of at least two different sizes encapsulated in a cavity with an inner diameter less than or equal to 10 nm, preferably less than or equal to 5 nm as a luminescent nanosystem. It is preferably used as a fluorescent nanosystem. In the use of these nanosystems the metal M of the AQCs is a transition metal or combination thereof. Preferably the transition metal is selected from Au, Ag, Co, Cu, Pt, Fe, Cr, Pd, Ni, Rh and combinations thereof, preferably is selected from Au, Ag, Cu and combinations thereof, and more preferably it is selected from Au, Ag and combination thereof.

In the scope of this invention the term "combination of transition metals" refers to AQCs having atoms of at least two different transition metals as well as to the presence of AQCs of a single transition metal in the presence of AQCs of another transition metal different from the first such that the at least two AQCs of different size can be AQCs with the same transition metal, AQCs with different transition metal, or AQCs with the same or different bimetal combination.

Figure 3:
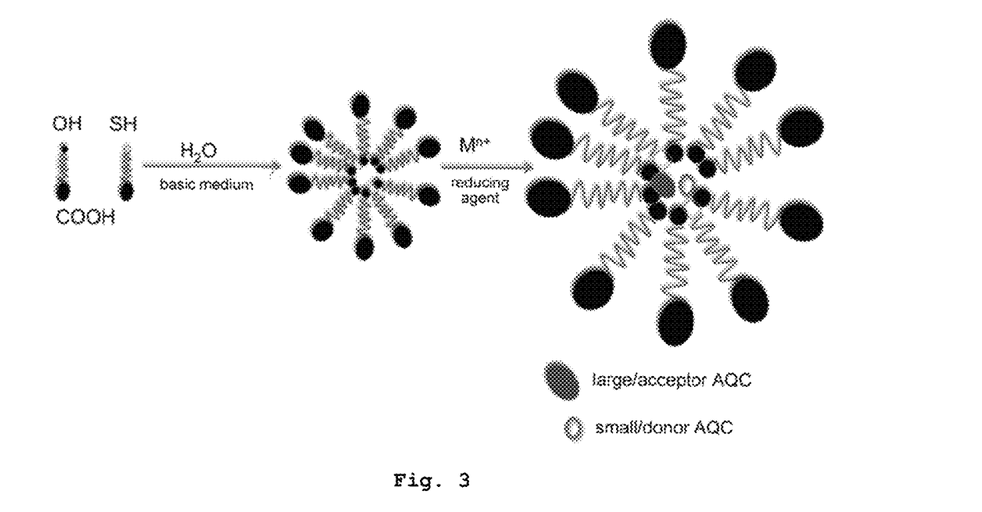
FIG. 3 shows a schematic depiction of the formation of the AQCs inside the nanosystem particularly inside the nanosomes of Examples 1 and 2. In a first step, the ω-hydroxyacids and ω-mercaptoacids in the presence of a basic medium form the nanosome in water. In a second step, the transition metal or combination of metals which will produce small AQCs or donors and large AQCs or acceptors by means of reduction, is added. The example is schematic showing only one AQC of each type, but there may be a varied number of both inside the cavity.

The presence of at least two different sizes in the interior nanocavity of AQCs is what allows using the nanosystems described as luminescent nanosystems. In a particular embodiment, the presence of OH and SH groups in the inner cavity of the nanosome allows selecting the production of the at least two types of clusters and their sizes, i.e., by varying the OH/SH ratio the size of the two types of clusters produced as schematically seen in FIGS. 2 and 3 can be selected.

The sizes of the clusters to be synthesized are determined by the [mercapto]/[M]=R1 and [hydroxyl]/[mercapto]=R2 concentration ratio.

The R1 ratio determines the size of the smaller cluster, the donor cluster, such that an increase of the ratio decreases the size of the smaller clusters produced ("arrested growth").

The R2 ratio determines the size of the larger cluster (acceptor cluster), such that an increase of this ratio increases the size of the larger clusters produced.

The expression "different size" of the AQCs refers to the fact that the at least two AQCs are different in number by at least three metal atoms. Preferably they are different by at least four metal atoms. More preferably they are different by at least five metal atoms.

Without being bound to any particular theory, it is believed that luminescence is produced by the Förster resonance energy transfer (FRET) involving the energy absorbance by a fluorophore at an excitation wavelength ($\lambda_{exc.}$) followed by the emission by another fluorophore at an emission wavelength ($\lambda_{em.}$) greater than the excitation wavelength, i.e., $\lambda_{em.} > \lambda_{exc.}$. The interaction to produce FRET only happens at very short distance, less than or equal to approximately 10 nm, between two electronic excitation states of two fluorescents molecules in which the emission wavelength of one of them coincides with the excitation wavelength of the other. This excitation energy is transferred through a dipole-dipole intermolecular bonding without radiation. Both wavelengths, $\lambda_{exc.}$ and $\lambda_{em.}$, are separated by tens or hundreds of nanometers. This wavelength difference is what is known as Stokes shift, $\delta_{stokes} = \lambda_{em} - \lambda_{exc.}$.

Figure 1:
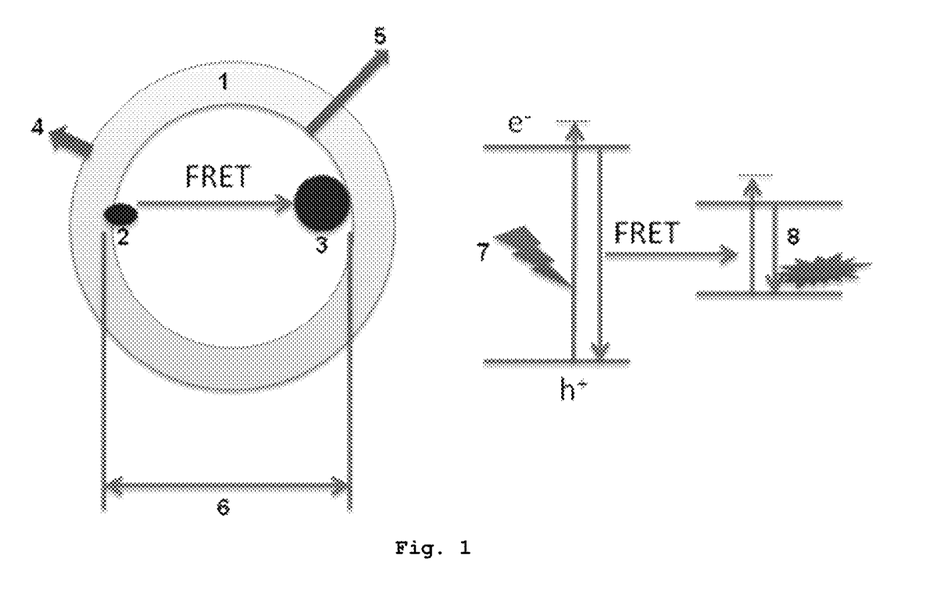
FIG. 1 shows a schematic depiction of the invention where the numbers refer to: 1. nanosystem; 2. small AQC or donor; 3. large AQC or acceptor; 4. functionalization of the outer surface of the nanosystem; 5. functionalization of the inner cavity; 6. inner diameter of the nanocavity which is within of the range of Förster distance of approximately 10 nm or less; 7. excitation of the electrons to higher energy levels ($\lambda_{exc.}$); 8. emission ($\lambda_{em.}$); and the arrow indicates the presence of Förster resonance energy transfer (FRET).

Therefore, in the scope of the present invention, in order to produce luminescence through Förster resonance energy transfer (FRET) between the AQCs of at least two different sizes, the smaller sized AQC or excitation cluster which acts like a donor AQC receives the external excitation at a particular excitation wavelength, it therefore goes into an excited electronic state. This excitation energy is transferred to the acceptor AQC or emission cluster which is at a distance less than or equal to 10 nm Foster distance, as schematically depicted in FIG. 1.

An approximate estimation of the cluster excitation and emission wavelengths can be determined by approximation by means of the Jellium model (see J. Calvo et al., *Encyclopedia of Nanotechnology*, Ed. by B. Bhushan, Springer Verlag, 2011, for example). This model predicts in a rather approximate manner the prohibited energy bandgap of the clusters and, therefore, the position of the emission bandgap thereof. The excitation bandgap of the clusters can in turn be predicted from the emission bandgap taking into account that the Stokes shift in clusters of a particular size is of approximate 50-100 nm. The following table, Table 1, shows the theoretical data for AQCs of Au or Ag according to this mode, i.e., the approximate excitation $\lambda_{exc.}$, and emission, $\lambda_{em.}$, wavelengths have been calculated with an error of ±50 nm in AQCs of Au or Ag by means of said Jellium model: $E_{em} = E_F/N^{1/3}$; where $E_{em}$=emission energy; N=no. of atoms in the AQC; and $E_F$=Fermi level which is the same approximately 5.5 eV for gold and silver.

TABLE 1

| Cluster | $\lambda_{exc.}$ (nm) | $\lambda_{em.}$ (nm) |
|---|---|---|
| $A_2$ | 200-250 | 300 |
| $A_3$ | 240-290 | 340 |
| $A_4$ | 270-320 | 370 |
| $A_5$ | 300-350 | 400 |
| $A_6$ | 325-375 | 425 |
| $A_7$ | 350-400 | 450 |
| $A_{10}$ | 400-450 | 500 |
| $A_{12}$ | 440-490 | 540 |
| $A_{15}$ | 475-525 | 575 |
| $A_{20}$ | 535-585 | 635 |
| $A_{25}$ | 580-630 | 680 |
| $A_{30}$ | 630-680 | 730 |
| $A_{40}$ | 700-750 | 800 |

These values can also vary in practice when the nanosystem is made to react to exchange the OH and SH groups with other ligands in the inner cavity of the nanosystem. Without being limiting, the ligands to be exchanged can be chosen from —NH$_2$, —NH—, —Cl, —PH$_3$, —SR, —OR, —NR$_2$, —NHR, —NR—, where R represents a short chain organic group capable of forming nanosomes.

In the context of the present invention, the luminescent nanosystems described present Stokes shifts greater than approximately 150 nm, preferably greater than approximately 300 nm.

In other words, the type of clusters to be used to obtain a particular excitation and emission wavelength can be decided from the table above. Thus, for example, to obtain a system with an excitation wavelength at 300 nm, an emission wavelength at 550 nm and a Stokes shift of 250 nm, the following cluster sizes should be selected:

excitation cluster ("donor"): $A_3/A_4$,
emission cluster ("acceptor"): $A_{12}$.

Therefore another aspect of the present invention relates to a method for detecting the nanosystems described which comprises the steps of:

a) exciting the nanosystem with an external excitation source at an excitation wavelength, $\lambda_{exc.}$, and
b) detecting one or more of the following parameters:
   emission wavelength ($\lambda_{em.}$),
   intensity,
   mean lifetime,
   anisotropy,
   of said nanosystem by suitable detection means.

In a preferred embodiment the method for detecting the nanosystem additionally comprises in that step b) for detecting one or more of the following parameters, emission wavelength, intensity, mean lifetime or anisotropy, is performed with a particular delayed time. This embodiment is based on the fact that the times of half life of the luminescence of the nanosystems of the invention are greater than 0.1 µs. The delayed time for detecting and measuring one or more of the parameters is greater than 0.1 µs and is preferably greater than 1 µs. Thus, possible interferences due to other emission wavelengths, $\lambda_{em}$ which can be created after excitation with an external excitation source at an excitation wavelength, $\lambda_{exc.}$ in addition to the emission wavelength of the nanosystem object of the present invention, are prevented.

"Exciting" is understood in the scope of the present invention as irradiating the nanosystem with a light radiation of a particular wavelength.

The "suitable detection means" relate to methods for detecting and optionally measuring the indicated parameters known by the person skilled in the art, i.e., methods for detecting the emission wavelength of the luminescence, particularly of the fluorescence, methods for detecting the intensity of the luminescence particularly of the fluorescence, methods for detecting the mean lifetime of the intensity of the luminescence or methods for detecting the anisotropy.

As no other molecules are present in the inner nanocavity of the nanosystem, the energy does not dissipate or lost, i.e., the luminescence is maintained. In a particular embodiment, there is no blinking or photobleaching for at least 500 minutes exciting the samples at 300 nm every 30 seconds.

Emission lifetime ($\tau$) which is the luminescence extinction time or the mean lifetime which is the time lapsed since the end of the excitation until the emission intensity reduces to 1/e of the maximum intensity value, i.e., until it reduces to approximately 37%, can be measured. In a embodiment of the present invention the mean lifetime of the luminescence, preferably fluorescence, is greater than 0.1 µs, preferably greater than 1 µs. In a particular embodiment, the nanosystems synthesized have an emission lifetime greater than microsecond for more than 37% of the fluorescence signal.

The nanosystems described have functional groups on the outside thereof, for example, the nanosomes have COOH groups that can be used to join covalently with proteins, nucleic acids, and other biomolecules. Therefore, another additional aspect due to this property relates to the use of the luminescent nanosystems of the invention as a fluorescent probe, biomarker or contrasting agent. These nanosystems can be used in biology systems both in vitro and in vivo.

Another additional aspect relates to the nanosystems comprising atomic quantum clusters (AQCs) of at least two different sizes encapsulated in a cavity with an inner diameter less than or equal to 10 nm, preferably less than or equal to 5 nm, wherein the metal of the AQCs is a transition metal with the exception of Au or a combination of transition metals in which Au can be included, and wherein the transition metal is preferably selected from Ag, Cu and a combination of transition metals. In a particular embodiment the cavity is the inner cavity of a nanosome comprising ω-hydroxyacids and ω-mercaptoacids and wherein the AQCs of at least two different sizes are characterized by being made up of:

between 2 and 309 metal atoms ($M_n$, $2 \leq n \leq 309$),
between 2 and 102 metal atoms ($M_n$, $2 \leq n \leq 102$),
between 2 and 55 metal atoms ($M_n$, $2 \leq n \leq 55$), and
between 2 and 25 metal atoms ($M_n$, $2 \leq n \leq 25$).

Another aspect of the invention relates to a method for obtaining the nanosystems described in the present invention comprising atomic quantum clusters (AQCs) of at least two different sizes encapsulated in a cavity with an inner diameter less than or equal to 10 nm, preferably less than or equal to 5 nm, wherein the metal of the AQCs is a transition metal with the exception of Au or a combination of transition metals, preferably the transition metal is selected from Ag, Cu and a combination of transition metals, which comprises the steps of:
a) preparing a nanosome by mixing ω-hydroxyacids and ω-mercaptoacids in the presence of a base in aqueous medium,
b) adding at least one metal salt to the mixture prepared in step a), and
c) reducing the mixture obtained in step b).

Tetrabutylammonium hydroxide, tetraoctylammonium hydroxide, triethylbenzylammonium hydroxide, tri-n-octyl-methylammonium hydroxide, trimethyldecylammonium hydroxide, tetramethylammonium hydroxide, tetraethylammonium hydroxide or any other hydroxide having a voluminous group such as a counterion, preferably tetrabutylammonium hydroxide can be used as a base in step a).

In step b) metal salts of transition metals or combinations thereof can be used. Non limiting examples of metal salts are nitrates, sulfates, sulfites, chlorides, bromides, iodides, phosphates, hydroxides, cyanates, carboxylates, thiomalates, thioglucosates of the transition metals. Examples of these metal salts to be used as a single metal salt or in combination with other metal salts are $AgNO_3$, $CH_3COOAg$, $Ag_3AsO_4$, $AgBrO_3$, $AgBr$, $Ag_2CO_3$, $AgClO_3$, $AgCl$, $AgCrO_4$, $AgOCN$, $AgIO_3$, $AgI$, $Ag_2O$, $AgClO_4$, $Ag_3PO_4$, $Ag_2SO_4$, $Ag_2S$, $Ag_2SO_3$, $CuSO_4$, $CuCl_2$, $CuBr_2$, $CuI_2$, $Cu_2S$, $CuSCN$, $CuCN$, $CuCO_3$, $Cu_2O$, $Cu(OH)_2$, $Cu(NO_3)_2$, $Cu(ClO_4)_2$, $Cu(HCO_2)_2$ or $Cu(CO_2CH_3)_2$. Non-limiting examples of gold metal salts to be used in combination, are $HAuCl_4$, $AuCl$, $AuCl_3$, $HAuCl_4$, $HAuCl_4.aq$, $KAuCl_4$, $LiAuCl_4$, $(CH_3)_2SAuCl$, $C_3H_9AuClP$, $C_6H_{15}AuClP$, $C_{18}H_{15}AuClP$, $C_8H_{11}AuClP$, $C_5H_5AuCl_3N$, $(C_4H_9)_3PAuCl$, $C_{27}H_{36}AuClN_2$, $C_{21}H_{12}AuClF_9P$, $C_{20}H_{27}AuClP$, $C_{33}H_{49}AuClP$, $C_{42}H_{63}AuClO_3P$, $C_{21}H_{24}AuClN_2$, $C_{35}H_{49}AuF_6NO_4PS_2$ or $(C_{20}H_{15}AuF_6NO_4PS_2).2C_7H_8$.

Non-limiting examples of reduction systems or reducing agents to be used in step c) for reducing the mixture obtained in step c) can be $NaBH_4$, DIBAH, LiAlH4, $N_2H_4$ or $SnCl_2$ and also gentler reducing agents such as sodium hypophosphite, amines, sugars, organic acids, polymers such as polyvinylpyrrolidone, UV-VIS radiation, ultrasounds and photoreduction.

As used herein, the term "approximately" means a slight variation from the specified value, preferably within 10 percent of the specified value. However, the term "approximately" may mean a greater variation tolerance depending on, for example, the experimental technique used. The person skilled in the art understands said variations of a specified value and they are within the context of the present invention. Furthermore, in order to provide a more precise description, some of the quantitative expressions provided in the present document are not described with the term "approximately". It is understood that, the term "approximately" is explicitly use or otherwise, each amount given in the present document attempts to refer to the actual given value, and it also attempts to refer to the approximation of such given value which would be reasonably deduced based on the common knowledge in the art, including equivalents and approximations due to experimental conditions and/or from measurement for such given value.

EXAMPLES

Example 1

Synthesis of Gold AQCs Nanosomes with a Stokes Shift of 300 nm

For this example the method schematically depicted in FIG. 3 was followed.

Figure 4:
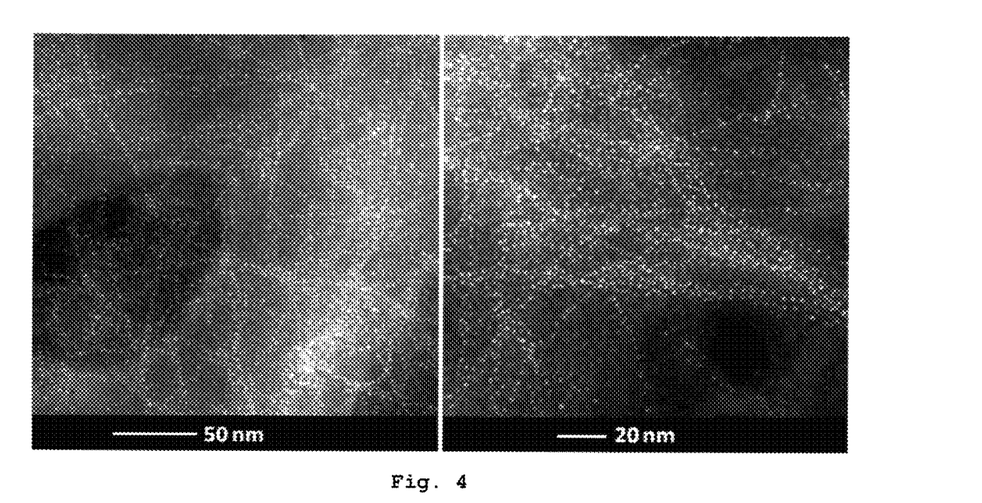
FIG. 4 shows the HAADF STEM electron microscopy images of the nanosystems obtained in Example 1, observing that the approximate size of the nanocavities containing the gold clusters is 1.5 nm.
Figure 5:
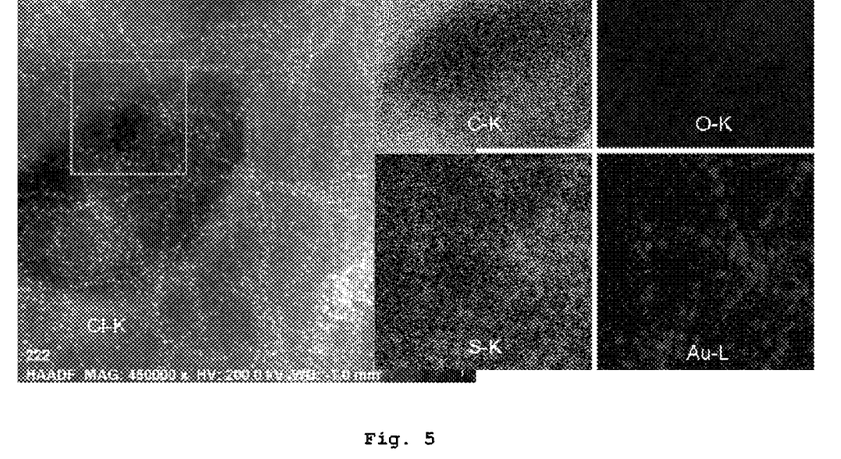
FIG. 5 shows the EDX Map of the images of FIG. 4 showing the composition of the nanosystems, observing that the gold clusters are protected by the molecules forming the nanosomes (C, O, S).
Figure 6:
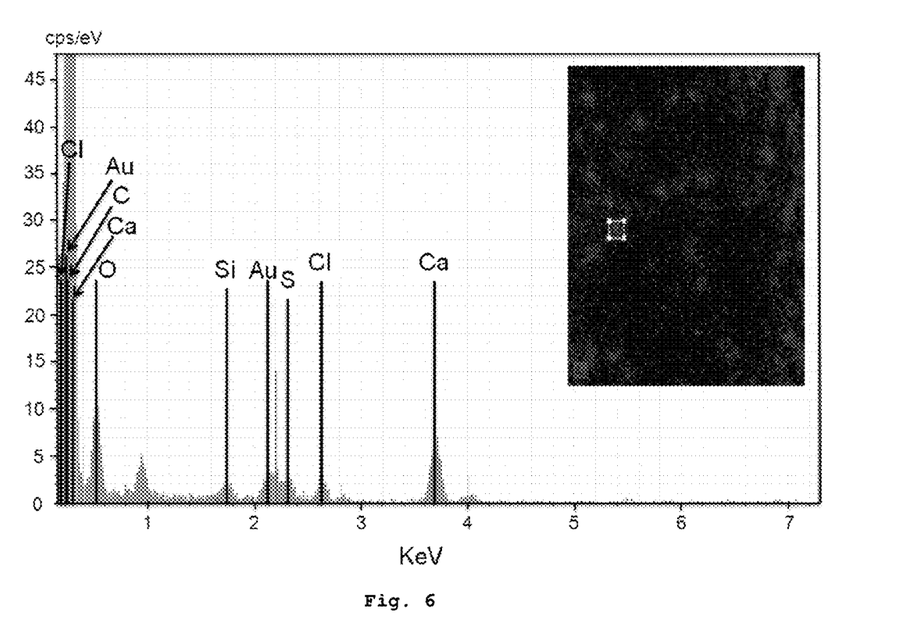
FIG. 6 shows the EDX Spectrum of an individual nanosystem extracted from the map above. The spectrum shows a significant signal of S and O in the region of the nanosystem indicating the presence of molecules containing these atoms (hydroxyl and mercapto acid of nanosome) protecting the Au clusters.
Figure 7:
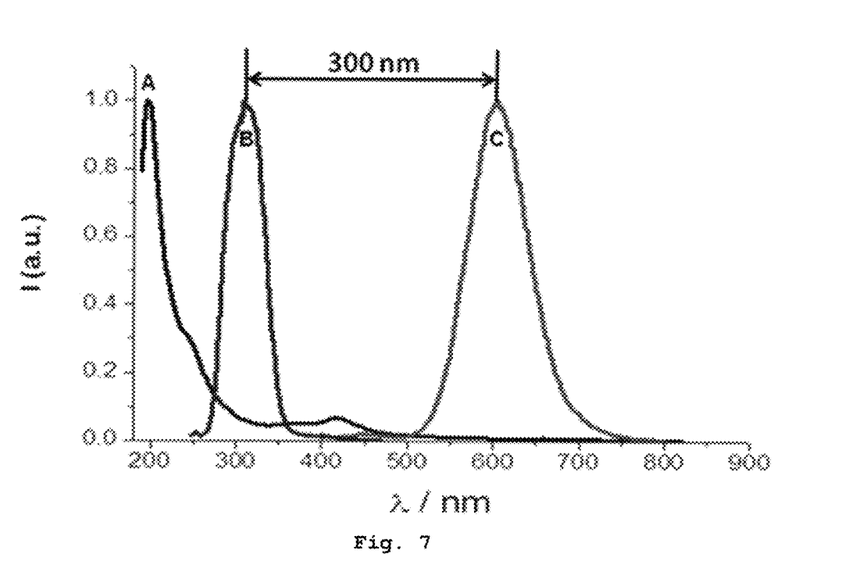
FIG. 7 shows the fluorescence of the nanosystems obtained in Example 1 where A is the absorbance; B is the excitation curve for emission at 600 nm, observing that it maximizes at an excitation wavelength of approximately 300 nm, and C is the emission curve for excitation at 300 nm, observing that it maximizes at a wavelength of approximately 600 nm. The results indicate a Stokes shift of 300 nm. The intensity, I is measured in arbitrary units (a.u.) and the wavelengths ($\lambda$) in nanometers (nm).

An aqueous solution of the 16-hydroxypalmitic acid (2 ml, mg/ml) was mixed with an aqueous solution of 16-mercaptopalmitic acid (0.622 ml, 10 mg/mL) with vigorous stirring in 5.4 ml of water and the necessary volume of tetrabutylammonium hydroxide until producing a basic mean. A volume of 400 µL of $HAuCl_4.3H_2O$ (Au (III) chloride hydrate, metal base at 99.999%, Aldrich) (5.8 mg/ml) solution was added to the resulting solution of nanosomes with subsequent reduction by means of adding 400 μL of a NaBH$_4$ solution (0.05 M). For the concentrations used, the values of R1 and R2 are 3.7 and 3.4, respectively. This gold nanosome stock solution was stirred at 35° C. for 1 hour. In order to purify the nanosomes containing the clusters, it is precipitated by adding acetic acid 0.5 M up to pH 7.8 and centrifuged to separate the solid containing excess reagents and nanosomes from the supernatant which contains the nanosomes with clusters. Finally, this supernatant is filtered through a filter of 0.45 microns. An electronic microscopy imageSTEM (scanning transmission electron microscopy) obtained by means of a Tecnai OSIRIS microscope equipped with HAADF (high angular annular dark field) and EDX (energy-dispersive X-ray spectroscopy) detectors, of the Au AQC nanosome samples obtained in the present example is shown in FIG. 4, it is observed that the approximate size of the nanocavities of the nanosomes containing the AQCs is approximately 1.5 nm. FIG. 5 shows the chemical analysis of FIG. 4 by means of EDX, it is observed that the Au clusters are protected by the molecules forming the nanosomes (C, O, S). FIG. 6 shows the EDX result of the typical analysis of one of the individual nanosomes observed in FIG. 4. The spectrum shows a significant S and O signal of in the region of the nanosystem which indicates the presence of molecules containing these atoms (hydroxyl and mercapto acid of the nanosome) protecting the Au clusters. Images of HR-STEM (high resolution) obtained with the same piece of equipment in turn show the complete absence of crystallinity characteristic of the presence of Au in the form of clusters (AQCs). FIG. 7 shows the absorption spectrum (measured with a Hewlett-Packard HP8452A spectrophotometer in a quartz cuvette of 1 mm×1 cm×3 cm), excitation spectrum and emission spectrum (measured with a Cary Eclipse Varian fluorescence spectrophotometer) of the Au AQC nanosomes, observing that they present maximum excitation at 300 nm and maximum emission at 600 nm which indicates a Stokes shift of 300 nm. The excitation at 300 nm in turn indicates, according to Table 1, that the excitation donor clusters present in the nanosomes have between 3 and 5 atoms, meanwhile the emission acceptor clusters have about 15 atoms.

Example 2

Synthesis of Au AQCs Nanosomes with a Stokes Shift of 370 nm

Figure 8:
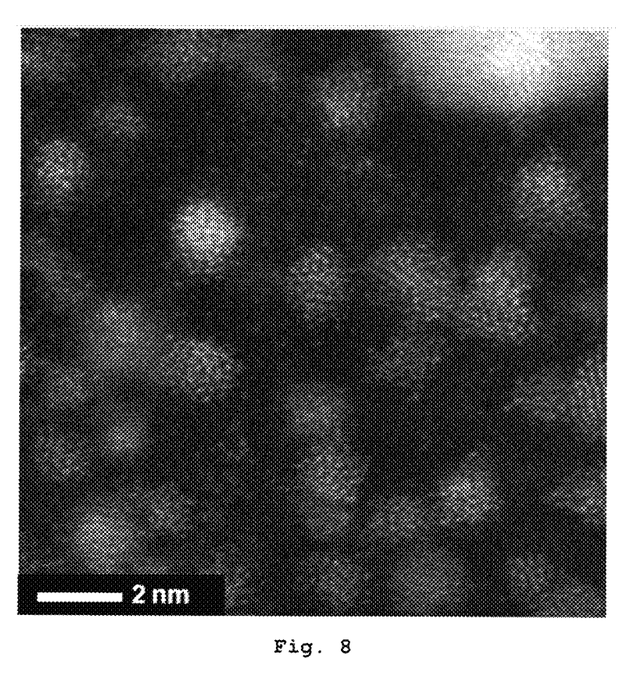
FIG. 8 shows the HAADF STEM electron microscopy images of the gold nanosystems obtained in Example 2. It is observed that the approximate inner diameter of the nanocavities containing the clusters is approximately 1.8 nm. Individual atoms of the clusters can also be observed inside the cavity.
Figure 9:
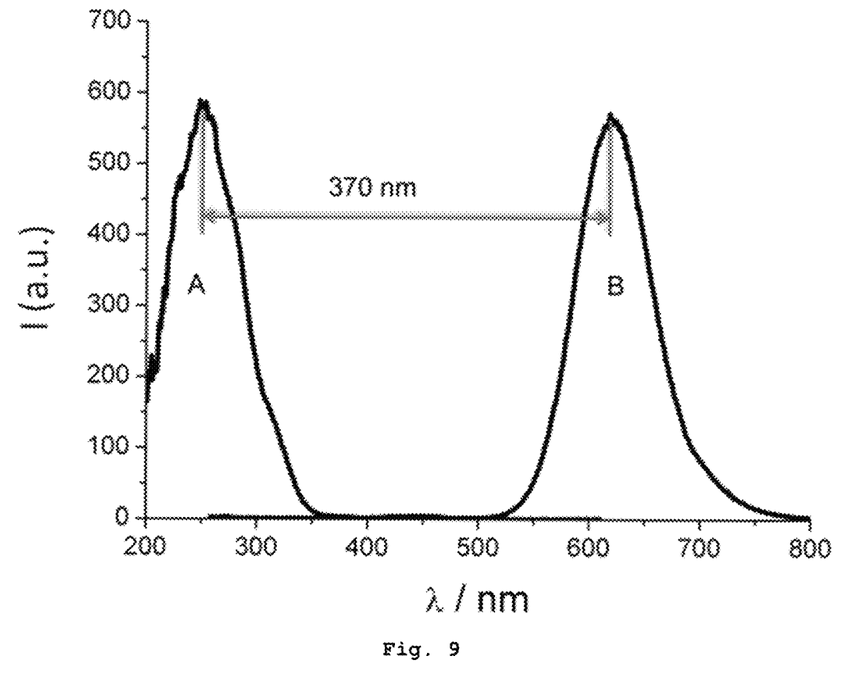
FIG. 9 shows the fluorescence of the nanosystems obtained in Example 2 where A represents the excitation curve for emission at 620 nm, observing that it maximizes at a excitation wavelength of approximately 250 nm, and B is the emission curve for excitation at 250 nm, observing that it maximizes at a wavelength of approximately 620 nm. The results indicate a Stokes shift of 370 nm. The intensity, I is measured in arbitrary units (a.u.) and the wavelengths ($\lambda$) in nanometers (nm).

In order to achieve a Stokes shift greater than that described in Example 1, it is necessary to reduce the size of the acceptor clusters and to increase that of the donors. As described in the specification this is achieved by increasing the values of R1 and R2 with respect to the values used in Example 1. The selected values in this example were R1=4.1 and R2=4.3. It then proceeded in the following manner. An aqueous solution of 16-hydroxypalmitic acid (2.52 ml, 10 mg/mL) was mixed with the aqueous solution of 16-mercaptopalmitic acid (0.622 ml, 10 mg/mL) with vigorous stirring in 4.9 ml of water and the necessary volume of tetrabutylammonium hydroxide until neutralization. A volume of 360 μL of a solution of HAuCl$_4$.3H$_2$O (Au (III) chloride hydrate, metal base at 99.999%, Aldrich) (5.8 mg/ml) was added to the resulting solution of nanosomes with subsequent reduction by means of adding 400 μL of a NaBH$_4$ solution (0.05 M). This gold nanosome stock solution was stirred at 25° C. for 30 minutes. In order to purify the nanosomes containing the clusters, they are precipitated by adding acetic acid 0.5 M up to pH 7.8 and centrifuged to separate the solid containing the excess reagents and nanosomes from the supernatant which contains the nanosomes with clusters. Finally, this supernatant is filtered through a filter of 0.45 microns. FIG. 8 shows a high resolution HAADF-STEM image obtained by means of a Jeol JEM-ARM200F microscope equipped with spherical aberration correction where the Au clusters of approximate size of 1.8 nm occupying the cavities of the nanosomes can be clearly seen. The image allows visualizing the atoms forming the clusters enclosed inside the nanocavities of the nanosomes. FIG. 9 shows the excitation and emission spectrums (measured with a Cary Eclipse Varian fluorescence spectrophotometer) of the Au AQC nanosomes, observing that they present maximum excitation at 250 nm and the maximum emission at 620 nm which indicates a Stokes shift of 370 nm. The position of the maximum excitation and emission in turns indicate, according to Table 1, that the donor Au clusters present in the nanosomes have between 2 and 3 atoms, meanwhile the emission acceptor clusters have about 20 atoms.

Example 3

Synthesis of Ag AQCs Nanosomes

Firstly, stock solutions of 16-mercaptopalmitic acid and 16-hydroxypalmitic acid are prepared at a concentration of 10 mg/ml, a given volume of tetrabutyl ammonium hydroxide solution (1.5 M in water) is added to ensure a molar ratio of fatty acid/TBAOH of 1. Then nanosomes are prepared mixing a given volume of each fatty acid stock solution with 25 ml of pure water (3.11 ml of 16-mercaptohexadecanoic acid and 10 ml of 16-hydroxyhexadecanoic acid).

In a second step, a stock solution of 0.0147 M AgNO$_3$ is prepared in pure water. Then 2.7 ml of this solution is poured in the nanosome sample. An extra amount of TBAOH solution is added to the mixture to ensure redispersion of the material. Then, 2.7 ml of a freshly prepared stock solution of 0.05 M NaBH$_4$ is added to the sample dropwise under vigorous agitation. The reaction is finished after 1 hour stirring at 35° C. in a thermostatted bath.

Example 4

Synthesis of Au AQCs Short-chain-length Nanosomes

Firstly, stock solutions of 12-mercaptododecanoic acid and 12-hydroxydodecanoic acid are prepared at a concentration of 10 mg/ml, a given volume of tetrabutyl ammonium hydroxide solution (1.5 M in water) is added to ensure a molar ratio of fatty acid/TBAOH of 1. Then nanosomes are prepared mixing a given volume of each fatty acid stock solution with 25 ml of pure water (3.11 ml of 12-mercaptododecanoic acid and 10 ml of 12-hydroxydodecanoic acid).

In a second step, a stock solution of 0.0147 M HAuCl$_4$ is prepared in pure water. Then 2.7 ml of this solution is poured in the nanosome sample. An extra amount of TBAOH solution is added to the mixture to ensure redispersion of the material. Then, 2.7 ml of a freshly prepared stock solution of 0.05 M NaBH$_4$ is added to the sample dropwise under vigorous agitation. The reaction is finished after 1 hour stirring at 35° C. in a thermostatted bath.

Example 5

Synthesis of Au AQCs Encapsulated by Inverse Micelles (Microemulsions)

Gold cluster encapsulated by inverse micelles (microemulsions) are prepared by mixing two different previous prepared microemulsions: one containing a $HAuCl_4$ salt and the other one containing $NaBH_4$.

The first microemulsion is prepared by dissolving 15.4 ml of Tergitol® 15S5, 1.37 ml of 1-butanethiol and 2.7 ml of an aqueous solution of $HAuCl_4$ (0.0147 M) in 80.6 ml of isooctane. The second microemulsion is prepared by dissolving 15.4 ml of Tergitol® 15S5, 1.37 ml of 1-butanethiol and 2.7 ml of an aqueous solution of $NaBH_4$ (0.05 M) in 80.6 ml of isooctane. Then, both microemulsions are mixed and the reaction is stirred during 24 h.

The invention claimed is:

1. A luminescent detection process, comprising disposing a luminescent nanosystem in a potential interaction environment, and luminescently detecting interaction of the luminescent nanosystem in said environment producing detectable luminescence, wherein said process comprises use of a nanosystem comprising metal atomic quantum clusters (AQCs) of at least two different sizes encapsulated in a cavity with an inner diameter less than or equal to 10 nm, as said luminescent nanosystem.

2. The process according to claim 1, wherein the cavity is the core of a nanosystem selected from the group formed by a nanosome, micelle and reverse micelle.

3. The process according to claim 2, wherein the cavity is the core of a nanosome, wherein the nanosome comprises ω-hydroxyacids and ω-mercaptoacids.

4. The process according to claim 1, wherein the metal AQCs of at least two different sizes are characterized by being made up of:
  between 2 and 309 metal atoms ($M_n$, $2 \leq n \leq 309$),
  between 2 and 102 metal atoms ($M_n$, $2 \leq n \leq 102$),
  between 2 and 55 metal atoms ($M_n$, $2 \leq n \leq 55$), or
  between 2 and 25 metal atoms ($M_n$, $2 \leq n \leq 25$).

5. The process according to claim 1, wherein the metals of the metal AQCs are transition metals or combinations thereof.

6. The process according to claim 1, wherein the luminescence is obtained after an excitation of the nanosystem by an external excitation source.

7. The process according to claim 1, wherein the luminescence is fluorescence.

8. The process according to claim 1, wherein the Stokes shift is greater than approximately 150 nm.

9. The process according to claim 1, wherein the luminescence has a decaying time greater than 0.1 μs.

10. The process according to claim 1, wherein the nanosystems is used as a fluorescent probe, biomarker or contrasting agent.

11. The process according to claim 1, wherein the cavity is an inner cavity of a nanosome.

12. The process according to claim 1, wherein the metal AQCs comprise metal selected from the group consisting of Au, Ag, Cu, and combinations thereof.

13. The process according to claim 1, wherein the metal AQCs comprise metal selected from the group consisting of Au, Ag, and combinations thereof.

14. The process according to claim 1, wherein the Stokes shift is greater than 300 nm.

15. The process according to claim 1, wherein the luminescence has a decaying time greater than 1 μs.

* * * * *

UNITED STATES PATENT AND TRADEMARK OFFICE
CERTIFICATE OF CORRECTION

PATENT NO. : 9,784,680 B2
APPLICATION NO. : 14/123149
DATED : October 10, 2017
INVENTOR(S) : Manuel Arturo Lopez Quintela

It is certified that error appears in the above-identified patent and that said Letters Patent is hereby corrected as shown below:

In the Specification

Column 10, Lines 61-62: "16-hydroxypalmitic acid (2 ml, mg/ml) was mixed" should be --16-hydroxypalmitic acid (2 ml, 10 mg/ml) was mixed--.

Column 11, Line 12: "microscopy imageSTEM" should be --microscopy image STEM--.

Signed and Sealed this
Second Day of January, 2018

Joseph Matal
*Performing the Functions and Duties of the*
*Under Secretary of Commerce for Intellectual Property and*
*Director of the United States Patent and Trademark Office*